United States Patent
McLuen

(10) Patent No.: US 10,207,285 B2
(45) Date of Patent: Feb. 19, 2019

(54) FLUID DISPENSING NOZZLE ASSEMBLY

(71) Applicant: Agilent Technologies, Inc., Santa Clara, CA (US)

(72) Inventor: Gary McLuen, Port Townsend, WA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 297 days.

(21) Appl. No.: 14/841,573

(22) Filed: Aug. 31, 2015

(65) Prior Publication Data

US 2016/0059236 A1    Mar. 3, 2016

Related U.S. Application Data

(60) Provisional application No. 62/043,962, filed on Aug. 29, 2014.

(51) Int. Cl.

| | |
|---|---|
| B05B 15/55 | (2018.01) |
| B05B 1/00 | (2006.01) |
| B05B 15/60 | (2018.01) |
| B01L 3/02 | (2006.01) |
| G01N 35/10 | (2006.01) |

(52) U.S. Cl.
CPC ............ B05B 15/55 (2018.02); B01L 3/0293 (2013.01); B05B 1/00 (2013.01); B05B 15/60 (2018.02); *B01J 2219/0036* (2013.01); *B01L 2200/025* (2013.01); *B01L 2200/0689* (2013.01); *G01N 35/1002* (2013.01)

(58) Field of Classification Search
CPC ....... B05B 15/025; B05B 15/55–15/60; B05B 1/00; B01L 3/0293; B01L 2200/025; B01L 2200/0689; G01N 35/1002; B01J 2219/0036

USPC .................................................. 239/106–119
See application file for complete search history.

(56) References Cited

U.S. PATENT DOCUMENTS

| | | | | |
|---|---|---|---|---|
| 5,960,530 A | * | 10/1999 | Kerr ...................... | B01L 3/0275 264/230 |
| 5,976,470 A | * | 11/1999 | Maiefski .............. | B01J 19/0046 222/485 |
| 5,996,576 A | * | 12/1999 | Yule ...................... | B05B 7/0807 128/203.12 |
| 2003/0109060 A1 | * | 6/2003 | Cook .................... | B01J 19/0046 436/180 |
| 2004/0173153 A1 | * | 9/2004 | Muramatsu ....... | H01L 21/67051 118/715 |
| 2012/0294780 A1 | * | 11/2012 | Bailey .................. | B01L 3/0241 422/511 |
| 2014/0224382 A1 | * | 8/2014 | Nuotio .................... | B01L 3/523 141/98 |

* cited by examiner

*Primary Examiner* — Darren W Gorman
*Assistant Examiner* — Juan C Barrera

(57) ABSTRACT

The current document is directed to a fluid dispensing nozzle assembly for use with a multi-well synthesizer and in other reagent distribution systems. In certain implementations, a fluid dispensing nozzle assembly comprises a nozzle body with a built-in dispenser tube, a reagent inlet tube, and a fitting that securely connects the inlet tube to the nozzle body. The nozzle body with the built-in dispenser tube and the reagent inlet tube are securely attached to one another by various coupling elements or adhesive material to ensure that liquid is transmitted through the inlet tube without leaking into the nozzle body and other undesired areas.

19 Claims, 5 Drawing Sheets

FLUID DISPENSING NOZZLE ASSEMBLY

CROSS-REFERENCE TO RELATED APPLICATION

This application claims the benefit of Provisional Application No. 62/043,962, filed Aug. 29, 2014.

TECHNICAL FIELD

The current document is directed to fluid dispensing nozzles and, in particular, to fluid dispensing nozzles that dispense reagents within an oligonucleotide synthesizer.

BACKGROUND

Scientific discoveries in molecular biology, genetics, and biochemistry have led to remarkable breakthroughs and innovations in research, genetic engineering, diagnostics, and a multitude of other research fields and commercial activities. Many of the technologies used in these fields involve synthetic biopolymers. Automated oligonucleotide synthesizers use fluid dispensing nozzles coupled to a reagent reservoir to deposit tiny amounts of specific liquid reagents into reaction wells in which DNA and RNA synthesis is carried out. The amount of reagent deposited into a reaction well should be accurately controlled, and fluid dispensing nozzles should be frequently cleaned, in order to produce oligonucleotides at purities needed for many research and diagnostics applications. Similar fluid dispensing nozzles are also employed in diagnostics instrumentation, analytical instruments, and other devices and instruments. Researchers and engineers continue to seek new designs for fluid dispensing nozzles for use in various types of instruments.

SUMMARY

The current document is directed to a fluid dispensing nozzle assembly for use with a multi-well synthesizer and in other reagent distribution systems. In certain implementations, a fluid dispensing nozzle assembly comprises a nozzle body with a built-in dispenser tube, a reagent inlet tube, and a fitting that securely connects the inlet tube to the nozzle body. The nozzle body with the built-in dispenser tube and the reagent inlet tube are securely attached to one another by various coupling elements or adhesive material to ensure that liquid is transmitted through the inlet tube without leaking into the nozzle body and elsewhere.

DETAILED DESCRIPTION

Figure 1:
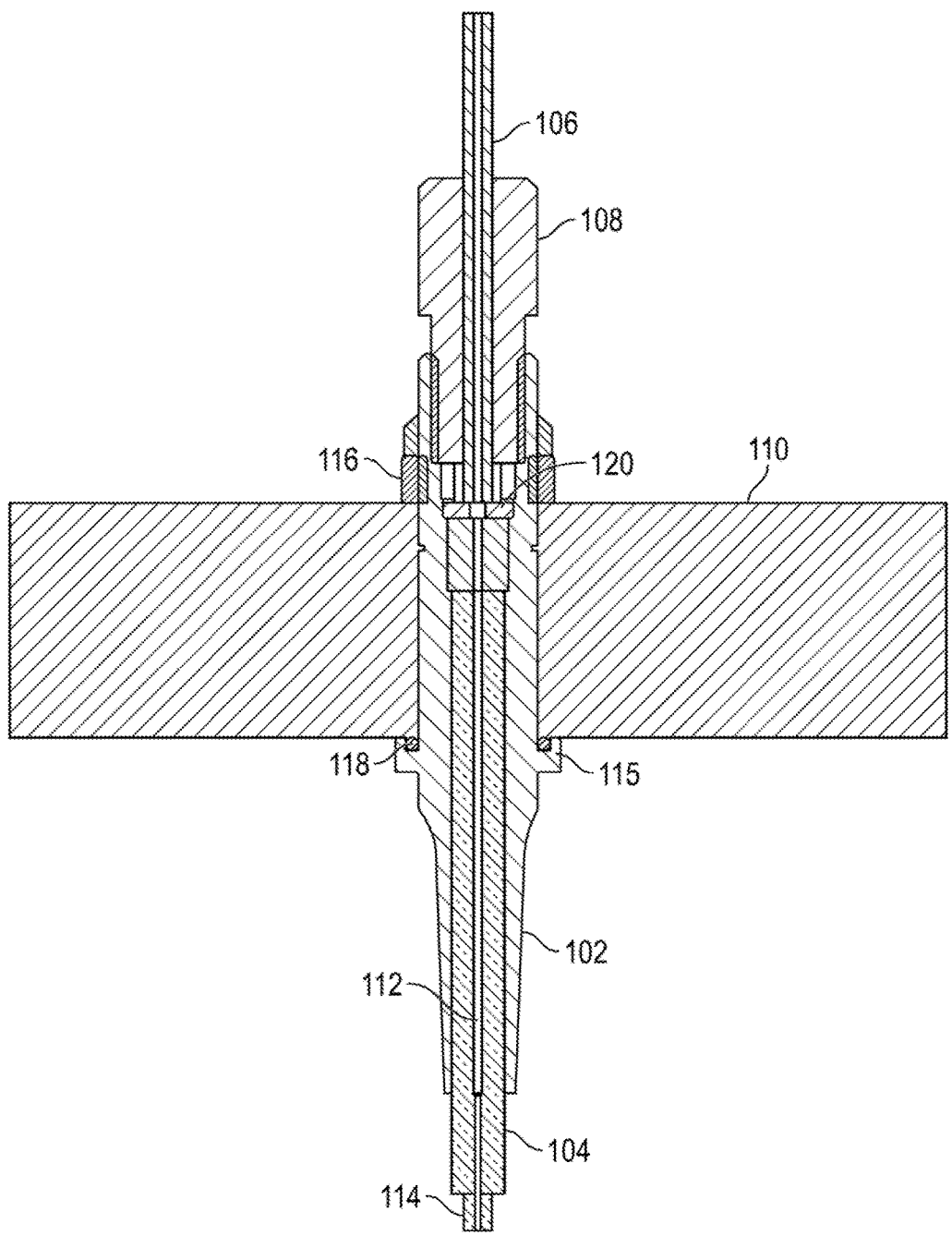
FIG. 1 provides a cross-sectional view of a fluid dispensing nozzle assembly.

FIG. 1 provides a cross-sectional view of a fluid dispensing nozzle assembly to which the current document is directed. The fluid dispensing nozzle assembly may be used with a multi-well synthesizer and with other reagent distribution systems to deliver precise amount of reagent to a well, vessel, or other fluid containers. The fluid dispensing nozzle assembly shown in FIG. 1 comprises a nozzle body 102 with a built-in dispenser tube 104, a reagent inlet tube 106, a fitting 108, and additional components discussed below. The fluid dispensing nozzle assembly is inserted, in one application, through a clear window plate 110 that is positioned, above a micro-titer plate having an array of reaction wells, by motor control within an automated oligonucleotide synthesizer. In certain implementations, sets of multiple nozzles arranged in an array in a clear window plate allow simultaneous delivery of multiple reagents. Alternatively, single nozzles can be used.

The built-in dispenser tube 104, made of glass or another suitable material, has a smooth inner bore 112 to allow clean, non-turbulent flow of fluid and has a square-edged tip 114 on one end to eliminate droplets building up due to surface tension of the dispensed reagent. Suitable materials are relatively unreactive with respect to the reagent solutions, sufficiently rigid to hold a precise shape, conducive to reagent-solution flow, and have similar additional desirable properties. The built-in dispenser tube 104 is affixed to the nozzle body using adhesive material, such as a silicone adhesive. The nozzle body 102 has a slightly larger inner bore near the top of the dispenser tube to provide space for adhesive material to be applied. Once the adhesive material securely affixes the dispenser tube to the nozzle body, the dispenser tube cannot be removed or detached from the nozzle body in a way that would allow the dispenser tube to be reused. The phrase "built-in" is used in this document to indicate that, in the described implementations, the dispenser tube cannot be removed or detached from the nozzle body in a way that would allow the dispenser tube to be reused. The nozzle body 102, including the built-in dispenser tube 104, is replaced as a unit when replacement is needed.

The nozzle body 102 is, in many implementations, made of an inert material, such as stainless steel, polyether ether ketone ("PEEK"), and various other polymeric, ceramic, metallic, and composite materials. The nozzle body has an internally threaded socket to receive an externally threaded fitting 108, such as an externally threaded flat-bottom fitting made by Upchurch Scientific, that connects the reagent inlet tube 106 to the nozzle body 102. The fitting 108, when screwed into the socket, forms an air-tight and liquid-tight seal between the inlet tube 106 and end of the dispenser tube 104. The nozzle body 102 has a circular flange 115 that rests against a bottom surface of the window plate 110 and has external threading on one end that engages with an internally threaded nut 116 so that the nozzle assembly can be securely fixed to the window plate 110 by vertical tension produced by upward force obtained by tightening the threaded nut 116 and the circular flange 115 pressing against the bottom surface of the window plate. A seal in the form of an O-ring 118 is disposed underneath the window plate 110 within the circular flange 115 to create an air-tight seal between the nozzle body and the window plate.

An adapter bushing 120 or other suitable element having an inner bore slightly larger than the inner bore 112 of the dispenser tube 104 and the inner bore of the inlet tube 106 is located above the end of the built-in dispenser tube to ensure that the inner bore reagent inlet tube 106 is positioned in alignment with the inner bore of the built-in dispenser tube 104. The adapter bushing 120 is made of an inert material. The fluid dispensing nozzle assembly shown in FIG. 1 enables liquid or other materials to be transmitted through the inlet tube and the built-in dispenser tube without leaking into the nozzle body and into other undesired areas.

Figure 2:
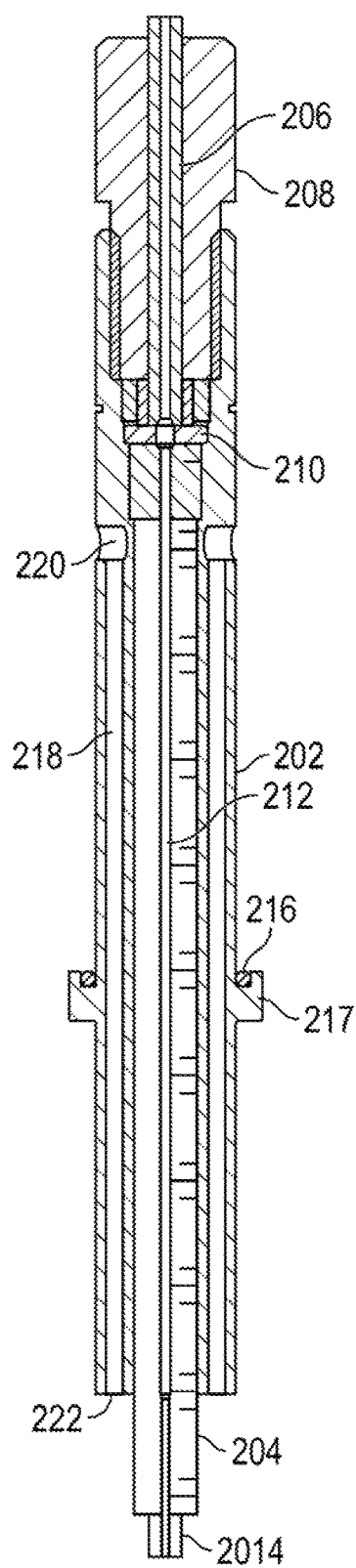
FIG. 2 provides a cross-sectional view of a second fluid dispensing nozzle assembly that includes an internal wash feature.

FIG. 2 provides a cross-sectional view of a second fluid dispensing nozzle assembly that includes an internal wash feature. During DNA/RNA synthesis, in a synthesizer employing multiple dispenser nozzles, some of phosphoramidite-dispensing nozzles are rarely used, as a result of which the dispense tips may dry out and become clogged. The second fluid dispensing nozzle shown in FIG. 2 has an internal wash feature that allows wash solvent to flow through the fluid dispensing nozzle body and clean the dispense tip.

Similar to the fluid dispensing nozzle assembly shown in FIG. 1, the second fluid dispensing nozzle shown in FIG. 2 comprises a nozzle body 202 with a built-in dispenser tube 204, a reagent inlet tube 206, and a threaded fitting 208 that securely connects the reagent inlet tube 206 to the nozzle body 202 to create an air-tight and liquid tight seal. An adapter bushing 210, similar to the adapter bushing 120 shown in FIG. 1, is disposed on the top of the built-in dispenser tube 204 to ensure that the inner bore of the reagent inlet tube 206 is vertically in alignment with the inner bore of the built-in dispenser tube 204. Similar to the nozzle body 102 shown in FIG. 1, the nozzle body 202 has a slightly larger bore near the top of the dispenser tube where the adapter bushing 210 is disposed in order to provide space for adhesive material to be applied. Once the adhesive material securely affixes the dispenser tube 204 to the nozzle body 202, the dispenser tube 204 cannot be removed or detached from the nozzle body 202 in a way that allows the dispenser tube to be reused. The built-in dispenser tube 204 has a smooth inner bore 212 to allow clean, non-turbulent flow of fluid and a square-edged tip 214 on one end to eliminate droplets building up due to surface tension of the dispensed reagent. Similar to the fluid dispensing nozzle assembly shown in FIG. 1, the second fluid dispensing nozzle is securely attached to a clear window plate by an O-ring 216 disposed within a circular flange 217 and a threaded nut (not shown in FIG. 2). In addition to the above-described features similar to those shown in FIG. 1, the second fluid dispensing nozzle includes a built-in cylindrical channel 218 for wash solvent. The internal wash feature comprises the wash-solvent channel 218, an inlet 220 through which the wash solvent flows into the wash-solvent channel, and an outlet 222 through which the wash solvents flows out of the wash-solvent channel.

Figure 3:
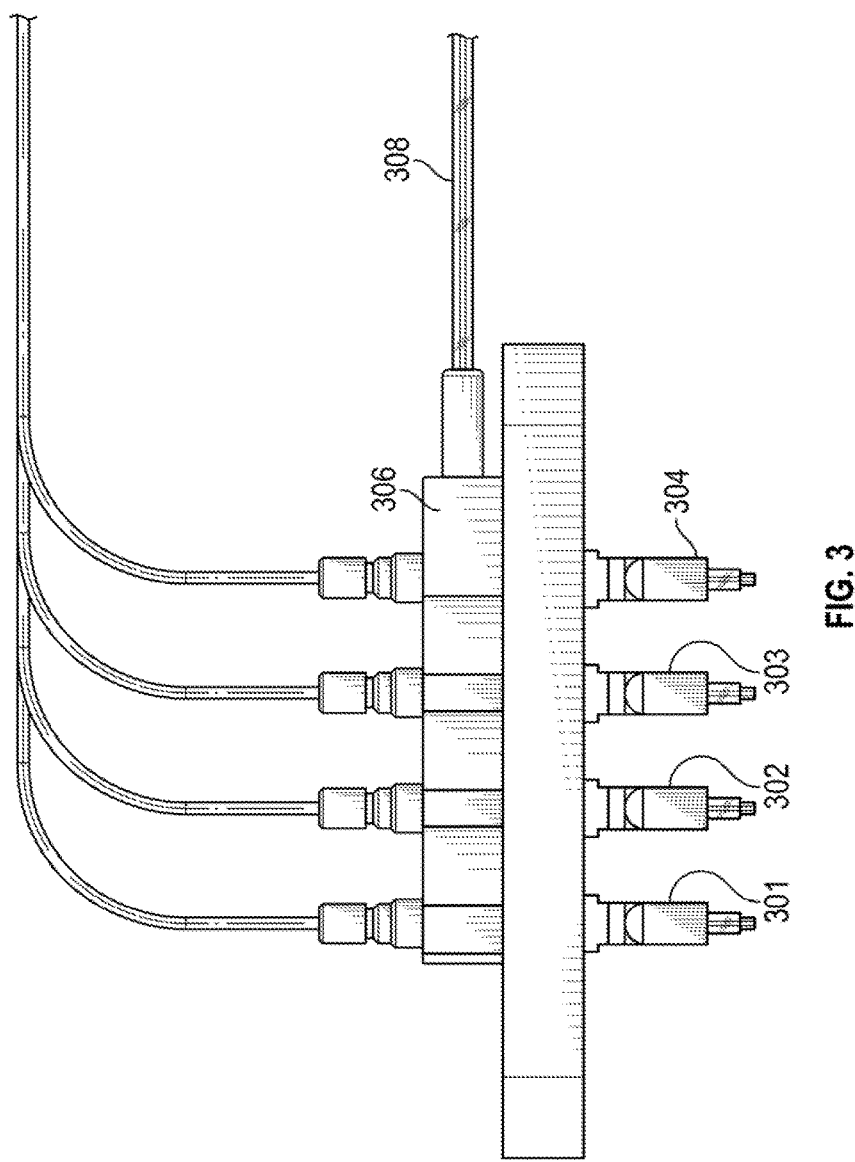
FIG. 3 provides a cross-section view of a nozzle-wash-manifold assembly.

FIG. 3 provides a cross-section view of a nozzle-wash-manifold assembly. The nozzle-wash-manifold assembly shown in FIG. 3 includes a plurality of fluid dispensing nozzles 301-304 of the type shown in FIG. 2 arranged in an array and attached to a distribution manifold 306 with a plurality of through-holes, into each of which a fluid dispensing nozzle of the type shown in FIG. 2 is inserted. The distribution manifold 306 includes an incoming vessel 308 horizontally connected to a wash solvent supply.

Figure 4A:
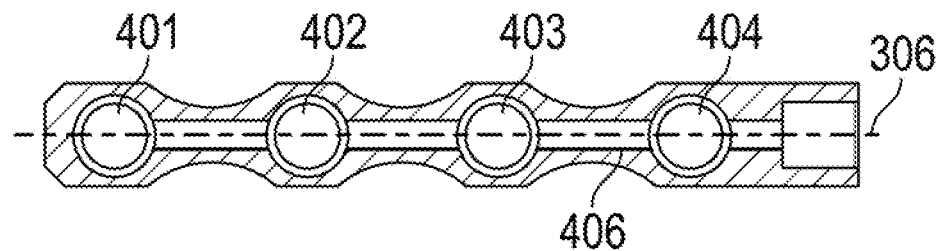
FIGS. 4A-C provide different views of the distribution manifold shown in FIG. 3.
Figure 4B:
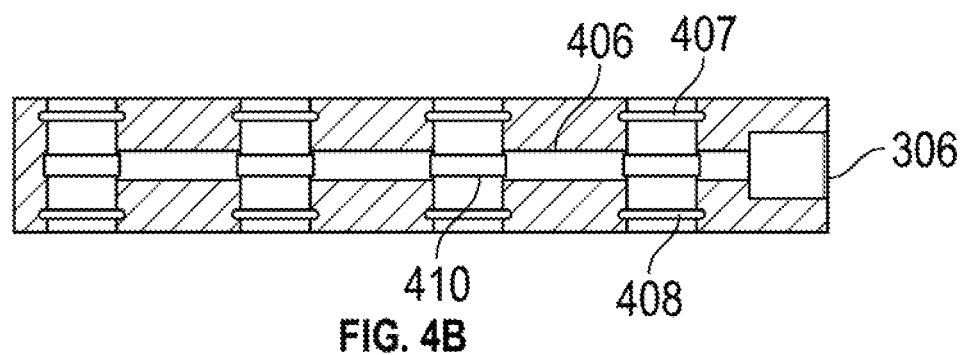
Figure 4C:
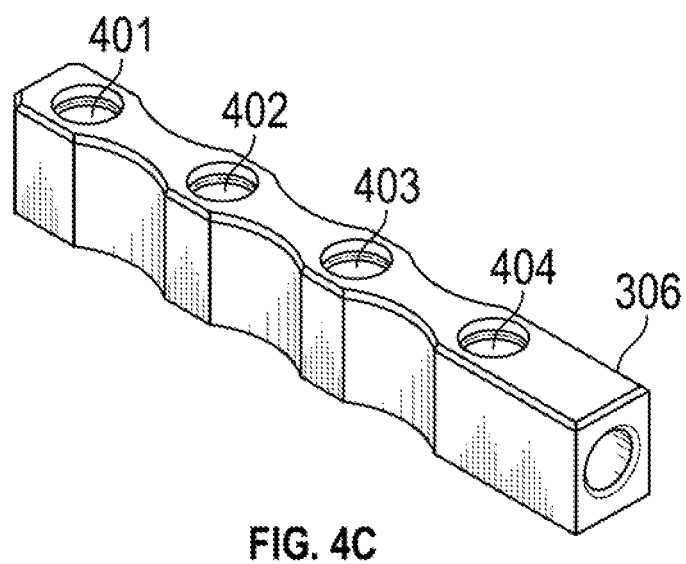

FIGS. 4A-C provide different views of the distribution manifold shown in FIG. 3. The distribution manifold 306 includes a plurality of vertical through-holes 401-404, each of which receives a fluid dispensing nozzle with an internal wash feature, and a horizontal inner bore 406 for delivery of wash solvent. The distribution manifold has two O-ring grooves 407-408 per fluid dispensing nozzle to create a liquid tight seal around the nozzle body. The horizontal inner bore 406 may form a groove 410 around each fluid dispensing nozzle to allow the wash solvent to flow into each nozzle body.

The nozzle-wash-manifold assembly shown in FIG. 3 is operated by flowing wash solvent through the incoming vessel 308 shown in FIG. 3 into the manifold 306. The wash solvent then passes through the horizontal bore 406 of the manifold that connects to the wash solvent inlet (220 in FIG. 2) of each nozzle to be evenly distributed through the wash solvent channel (218 in FIG. 2) of each nozzle. As the wash solvent leaves the wash solvent channel through the outlet (222 in FIG. 2), the wash solvent flows over the dispense tips 214 into a waste trough to be purged from the synthesizer.

Figure 5A:
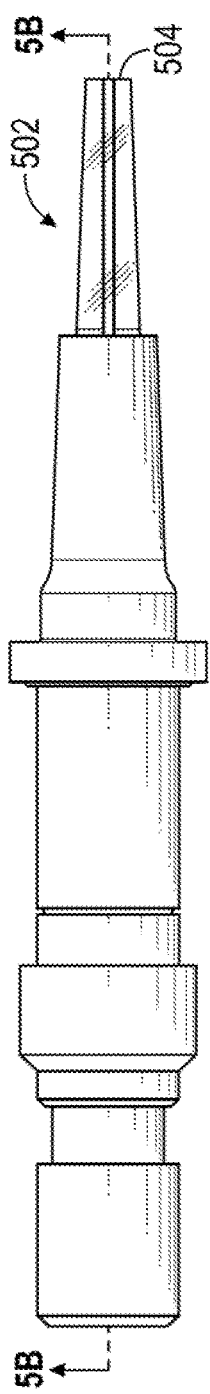
FIGS. 5A-B shown an additional, third implementation of a fluid dispensing nozzle assembly.
Figure 5B:
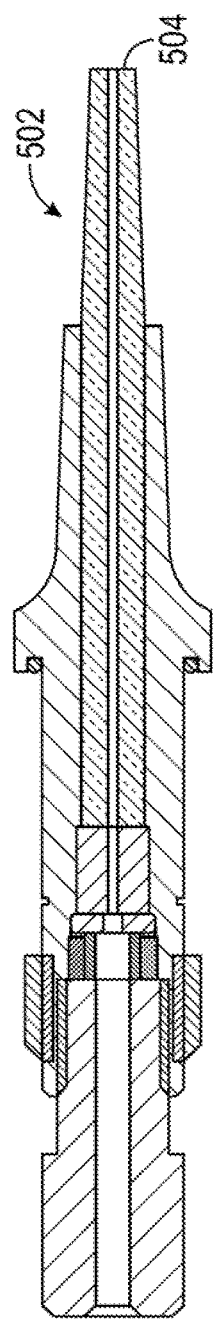

FIGS. 5A-B shown an additional, third implementation of a fluid dispensing nozzle assembly. FIG. 5A provides an external view of the third implementation of the fluid dispensing nozzle and FIG. 5B provides a cross-sectional view of the third implementation of the fluid dispensing nozzle. The third implementation of the fluid dispensing nozzle differs from both the first and second implementations of the fluid dispensing nozzles, shown in FIGS. 1 and 2, by having a dispenser tube with a tapered end 502 and sharp-edged dispense tip 504 at the tapered end. In one implementation, the dispense-tip end of dispenser tube has a 5° taper.

Although the present disclosure has been described in terms of particular implementations, it is not intended that the disclosure be limited to these implementations. Modifications within the spirit of the disclosure will be apparent to those skilled in the art. For example, the taper angle of the built-in dispenser tube may differ in different implementations, as may the dimensions and relative sides of various components.

It is appreciated that the previous description of the disclosed implementations is provided to enable any person skilled in the art to make or use the present disclosure. Various modifications to these implementations will be readily apparent to those skilled in the art, and the generic principles defined herein may be applied to other implementations without departing from the spirit or scope of the disclosure. Thus, the present disclosure is not intended to be limited to the implementations shown herein but is to be accorded the widest scope consistent with the principles and novel features disclosed herein.

The invention claimed is:

1. A fluid dispensing nozzle assembly that dispenses a reagent fluid input to the fluid dispensing nozzle assembly, the fluid dispensing nozzle assembly comprising:
   a nozzle body;
   a built-in dispenser tube that dispenses the reagent fluid, the built-in dispenser tube is mounted within and affixed to the nozzle body, the built-in dispenser tube includes a first end and a second end, the second end of the built-in dispenser tube defines a dispense tip that dispenses the reagent fluid;
   a reagent inlet tube, mounted to and within the nozzle body, a first end of the reagent inlet tube external to the nozzle body and a second end of the reagent inlet tube fluidly coupled to the first end of the built-in dispenser tube through an adapter bushing having an inner bore slightly larger than an inner bore of the built-in dispenser tube and an inner bore of the reagent inlet tube; and
   a wash-solvent channel that allows a wash solvent to flow over the dispense tip defined by the built-in dispenser tube that dispenses the reagent fluid.

2. The fluid dispensing nozzle assembly of claim 1 wherein the dispense tip that dispenses the reagent fluid has squared edges to eliminate droplets building up due to surface tension of the dispensed reagent.

3. The fluid dispensing nozzle assembly of claim 1 wherein the dispense tip has a smaller outer diameter than an outer diameter of the built-in dispenser tube.

4. The fluid dispensing nozzle assembly of claim 1 wherein the built-in dispenser tube is tapered to the smaller-outer-diameter second end of the built-in dispenser tube.

5. The fluid dispensing nozzle assembly of claim 1 wherein the built-in dispenser tube is made of glass or another material that does not appreciably react with the reagent fluid, is sufficiently rigid to hold a precise shape, and is conducive to reagent-solution flow.

6. The fluid dispensing nozzle assembly of claim 1 wherein the inner bore of the built-in dispenser tube is smooth to allow clean, non-turbulent flow of reagent fluid.

7. The fluid dispensing nozzle assembly of claim 1 wherein the built-in dispenser tube is affixed to the nozzle body by a silicone adhesive to prevent liquid flowing through the built-in dispenser tube from leaking into the nozzle body.

8. The fluid dispensing nozzle assembly of claim 1 wherein the nozzle body is made from an inert material selected from among:
- stainless steel;
- polyether ether ketone;
- another polymeric material;
- a ceramic material;
- another metallic material; and
- a composite material.

9. The fluid dispensing nozzle assembly of claim 1 wherein the nozzle body has an internally threaded socket to receive an externally threaded fitting that connects the reagent inlet tube to the nozzle body.

10. The fluid dispensing nozzle assembly of claim 9 wherein the externally threaded fitting is an externally threaded flat-bottom fitting.

11. The fluid dispensing nozzle assembly of claim 10 wherein, when the externally threaded fitting is screwed into the internally threaded socket, an air-tight and liquid-tight seal is formed between the second end of the inlet tube and the first end of the dispenser tube.

12. The fluid dispensing nozzle assembly of claim 1 wherein the nozzle body has a circular flange and has external threading on a first end that engages with an internally threaded nut.

13. The fluid dispensing nozzle assembly of claim 12 further including an O-ring within the circular flange that creates an air-tight seal between the nozzle body and an external surface.

14. The fluid dispensing nozzle assembly of claim 13 wherein the dispensing nozzle is mounted to an external plate through a circular hole in the external surface, the circular flange and O-ring sealing the nozzle body to a bottom surface of the external plate and the internally threaded nut securing the fluid dispensing nozzle assembly to an upper surface of the external plate.

15. The fluid dispensing nozzle assembly of claim 1 wherein the adapter bushing is made of a material that does not appreciably react with the reagent fluid.

16. The fluid dispensing nozzle assembly of claim 1 wherein coupling of the second end of the reagent inlet tube to the first end of the built-in dispenser tube through the adapter bushing provides, an air-tight and liquid-tight seal between the inlet tube and the dispenser tube.

17. The fluid dispensing nozzle assembly of claim 1 farther including an internal wash feature that includes the wash-solvent channel.

18. The fluid dispensing nozzle assembly of claim 17 wherein the internal wash feature further includes:
- an inlet through Which the Wash solvent flows into the wash-solvent channel; and
- an outlet through which the wash solvents flows out of the wash-solvent channel and over the dispense tip.

19. The fluid dispensing nozzle assembly of claim 17 wherein the fluid dispensing nozzle assembly is mounted within a wash-solvent distribution manifold.

* * * * *